United States Patent
Uematsu (10) Patent No.: US 9,149,443 B2
(45) Date of Patent: Oct. 6, 2015

(54) TAPE PREPARATION

(75) Inventor: Masanori Uematsu, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 13/519,440

(22) PCT Filed: Dec. 14, 2010

(86) PCT No.: PCT/JP2010/072451
§ 371 (c)(1),
(2), (4) Date: Aug. 28, 2012

(87) PCT Pub. No.: WO2011/081017
PCT Pub. Date: Jul. 7, 2011

(65) Prior Publication Data
US 2012/0316519 A1    Dec. 13, 2012

(30) Foreign Application Priority Data
Dec. 28, 2009  (JP) ................................. 2009-297872

(51) Int. Cl.
A61F 13/02 (2006.01)
A61K 9/70 (2006.01)
A61F 13/00 (2006.01)
A61M 35/00 (2006.01)

(52) U.S. Cl.
CPC ............. *A61K 9/7084* (2013.01); *A61K 9/7038* (2013.01); *A61F 13/02* (2013.01); *A61F 2013/0071* (2013.01); *A61F 2013/00851* (2013.01); *A61M 35/00* (2013.01)

(58) Field of Classification Search
CPC ... A61M 35/00; A61K 9/7038; A61K 9/7084; A61F 2013/0071; A61F 2013/00851; A61F 13/02
USPC ................................................... 604/304–308
See application file for complete search history.

(56) References Cited

U.S. PATENT DOCUMENTS

| | | | |
|---|---|---|---|
| 5,429,592 A * | 7/1995 | Jensen | 602/59 |
| 6,365,793 B1 * | 4/2002 | McLaughlin et al. | 604/359 |
| 7,078,582 B2 * | 7/2006 | Stebbings et al. | 602/57 |
| 8,021,347 B2 * | 9/2011 | Vitaris et al. | 604/304 |
| 8,235,949 B2 * | 8/2012 | Hack et al. | 604/180 |

(Continued)

FOREIGN PATENT DOCUMENTS

| | | |
|---|---|---|
| JP | 2002-47175 A | 2/2002 |
| JP | 2003-62058 A | 3/2003 |

(Continued)

*Primary Examiner* — Philip R Wiest
*Assistant Examiner* — Ariana Zimbouski
(74) *Attorney, Agent, or Firm* — Crowell & Moring LLP (57) ABSTRACT

A tape preparation is provided which does not use a backing such as a plastic film, knit or a woven fabric, or a nonwoven fabric, has very high conformability to skin, and is easy to use at the time of application. There is provided a tape preparation 1 that is produced by laminating a drug-containing adhesive layer 4 on the printed ink layer 3 side of a cover film 2 with printing thereon and covering the drug-containing adhesive layer with a release film 5. In this tape preparation, the adhesive strength between the cover film and the printed ink layer is higher than the adhesive strength between the drug-containing adhesive layer and the release film, and the adhesive strength between the printed ink layer and the drug-containing adhesive layer is higher than the adhesive strength between the cover film and the printed ink layer.

9 Claims, 4 Drawing Sheets

(56) References Cited

U.S. PATENT DOCUMENTS

| | | |
|---|---|---|
| 2003/0049440 A1 | 3/2003 | Kuroda et al. |
| 2010/0280468 A1* | 11/2010 | Haggstrom et al. ........... 604/318 |
| 2012/0123220 A1* | 5/2012 | Iyer et al. ...................... 600/300 |
| 2013/0172428 A1* | 7/2013 | Audett et al. ............... 514/772.6 |

FOREIGN PATENT DOCUMENTS

| | | |
|---|---|---|
| JP | 2006-160606 A | 6/2006 |
| JP | 2006-225522 A | 8/2006 |

* cited by examiner

TAPE PREPARATION

TECHNICAL FIELD

The present invention relates to tape preparations. Specifically, the present invention relates to a tape preparation that, when applied onto a joint part, which is a bendable part of a human body, or an uneven part, conforms to the movement of these parts and does not peel off easily, for example, by sweating.

BACKGROUND ART

Various tape preparations that are applied onto the surface of a human body for the purpose of anti-inflammation, pain relief, pruritus, shaking off drowsiness, refreshment, and the like have been previously launched.

These tape preparations are applied onto a wide variety of sites depending on their purposes. The tape preparations are often applied onto bendable parts such as an elbow joint or a knee joint, or curved parts such as a face, a neck, or a shoulder.

Figure 7:
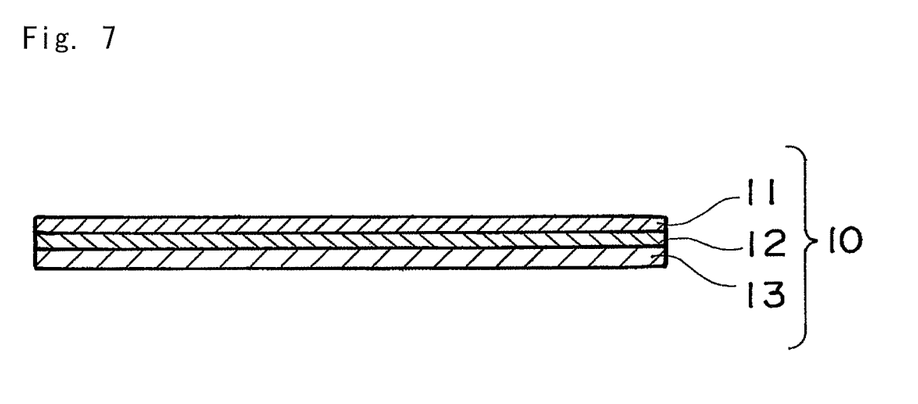
FIG. 7 is a schematic cross-sectional side view of a conventional tape preparation.

A conventional tape preparation is, as is shown in FIG. 7, a tape preparation 10 that includes a backing 11 on which a drug-containing adhesive layer (ointment layer) 12 is laminated and a release film 13 that covers the drug-containing adhesive layer (ointment layer) 12.

When the conventional tape preparation is applied in practice, the release film 13 is peeled off and the ointment layer is applied together with the backing. To enhance conformability at an application site, elastic materials such as a polyvinyl chloride film or a polyester film, a knit or a textile, or a nonwoven fabric are used as the backing on which the ointment layer is laminated.

The thickness of the backing of this tape preparation is thin in order to ensure conformability. The thickness is about 100 to 200 μm in the case of a film and about 700 to 1200 μm in the case of a nonwoven fabric or a knit.

Furthermore, the backing used for the tape preparation is very flexible. Therefore, people frequently fail in applying the tape preparation, since the tape preparation becomes difficult to handle at the stage when people peel off the release sheet and try to apply the tape preparation.

For this reason, conformability at an application site has been searched for while ensuring a certain amount of hardness of the backing. However, the tape preparation is not conformable to the complicated movement of skin and often causes an uncomfortable feeling at the time of application.

Another problem that has also been seen is that creases due to shrinking occur, which is unique to a tape preparation, and the applied tape preparation tends to peel off easily at its ends.

Furthermore, when a polyvinyl chloride film, a polyester film, and the like are used as the backing, their sealing performance causes sweating and consequently the tape preparation may peel off.

Therefore, development of a tape preparation that solves these problems has been under study in various ways (Patent Documents 1 to 4).

These studies mainly focus on a drug-containing adhesive layer. These problems are avoided, for example, by designing a highly adhesive preparation, but are not completely solved. Conversely, adverse effects such as damaged keratin and internal hemorrhage have been seen when the tape preparation is peeled off from an affected area.

PRIOR ART DOCUMENTS

Patent Documents

Patent Document 1: Japanese Patent Application Laid-Open No. 2002-047175

Patent Document 2: Japanese Patent Application Laid-Open No. 2003-062058

Patent Document 3: Japanese Patent Application Laid-Open No. 2006-160606

Patent Document 4: Japanese Patent Application Laid-Open No. 2006-225522

As described above, the conventional tape preparation has had the following problems:

(1) The tape preparation peels off easily at its ends when applied onto, for example, a joint part.
(2) The tape preparation peels off easily, for example, through sweating.
(3) A highly elastic and flexible backing is difficult to handle and often causes failure in application of the tape preparation.
(4) The tape preparation has poor conformability to an affected area and causes a rash or leaves a mark at the application site.
(5) Searching for good conformability to an affected area results in an expensive backing.

Originally, a tape preparation has the best conformability to skin when only a drug layer is applied onto a targeted affected area. However, applying only a drug layer leads to not only many failures in application but also problems after application caused by its adhesive power such as adhesion to clothes and the adhesion of dust or hair. There is also concern that the drug layer peels off (unexpectedly falls off). Therefore, a tape preparation by which only a drug layer is applied has not been realized so far.

SUMMARY OF THE INVENTION

Problems to be Solved by the Invention

Therefore, the present invention solves the conventional problems described above. It is an object of the present invention to provide a tape preparation that does not include a conventionally used backing such as a polyvinyl chloride film or a polyester film, a knit or a woven fabric, or a nonwoven fabric; that has very high conformability to skin; that is also easy to use at the time of application irrespective of sex or age; and moreover, that can be manufactured without changing a conventional production line at all.

As a result of intensive studies to solve these problems, the present inventor has found that a very good tape preparation with excellent conformability is produced by laminating a drug-containing adhesive layer on a cover film with printing thereon instead of a conventional backing so that a printed ink layer of the cover film with printing thereon serves as a covering layer for the applied drug-containing adhesive layer. Thus, the present inventor has completed the present invention.

In particular, the present invention provides a tape preparation that utilizes a printed ink layer instead of a conventional backing layer, wherein the printed ink layer covers a drug layer.

Means for Solving the Problem

Therefore, the basic aspect of the present invention to solve these problems is a tape preparation produced by laminating a drug-containing adhesive layer on a printed ink layer side of a cover film with printing thereon and covering the drug-containing adhesive layer with a release film.

More specifically, the present invention provides a tape preparation described above, wherein the adhesive strength between the cover film and the printed ink layer is higher than the adhesive strength between the drug-containing adhesive layer and the release film, and the adhesive strength between the printed ink layer and the drug-containing adhesive layer is higher than the adhesive strength between the cover film and the printed ink layer.

Thus, the present invention provides a tape preparation described above, wherein the drug-containing adhesive layer is applied onto an application site in such a manner that the printed ink layer is still laminated on the drug-containing adhesive layer, by peeling off the release film and applying the tape preparation, and then peeling off the cover film with printing thereon.

More preferably, the present invention provides a tape preparation that includes a slit on the cover film and/or the release film to make it easy to peel off the cover film from the printed ink layer or to peel off the release film from the drug-containing adhesive layer.

Therefore, the present invention specifically provides a tape preparation described above that is produced by laminating the drug-containing adhesive layer on the printed ink layer side of the cover film with printing thereon and covering the drug-containing adhesive layer with the release film, wherein application is completed by peeling off the release film, then applying the drug-containing adhesive layer onto an applied surface, and then peeling off the cover film.

In another aspect, the present invention also provides a method of use of the tape preparation described above, wherein application is completed by peeling off the release film and applying the drug-containing adhesive layer onto a targeted surface, and then, moreover, peeling off the cover film.

Effects of the Invention

The present invention as described above can produce the following advantageous effects.

Specifically, in the tape preparation of the present invention:
(1) The printed ink layer is thinner than a currently used backing and therefore does not inhibit the original resilience and elasticity that the drug-containing adhesive layer (ointment layer) has.

Accordingly, conformability of the tape preparation at an application site is very good.
(2) The printed ink layer also conforms to the elasticity of the drug-containing adhesive layer (ointment layer). Therefore, the tape preparation does not peel off from an application site, while a conventional backing causes this.
(3) The printed ink layer has moisture permeability unlike a conventional film backing and therefore does not cause sweating at an application site. Furthermore, the tape preparation does not peel off easily even when it is applied when sweating in summer.
(4) Due to good conformability at an application site, it is not necessary to increase the adhesiveness of the drug-containing adhesive layer (ointment layer). Therefore, a load at the application site is reduced and a mark is less prone to be left at the application site.
(5) In the case of applying the tape preparation at an application site, the rigidity of the cover film makes it easy to handle the tape preparation itself. Therefore, there are less failures in applying the tape preparation.
(6) The tape preparation can be processed without changing a conventional production line and also does not need an expensive raw material, especially an expensive backing. Therefore, the tape preparation has the advantage of being able to reduce costs.

EMBODIMENTS FOR CARRYING OUT THE INVENTION

As described above, the basic embodiment of the present invention is a tape preparation produced by laminating a drug-containing adhesive layer on a printed ink layer side of a cover film with printing thereon and covering the drug-containing adhesive layer with a release film.

In other words, the tape preparation of the present invention is produced by using a printed ink layer instead of a conventional backing layer.

Figure 1:
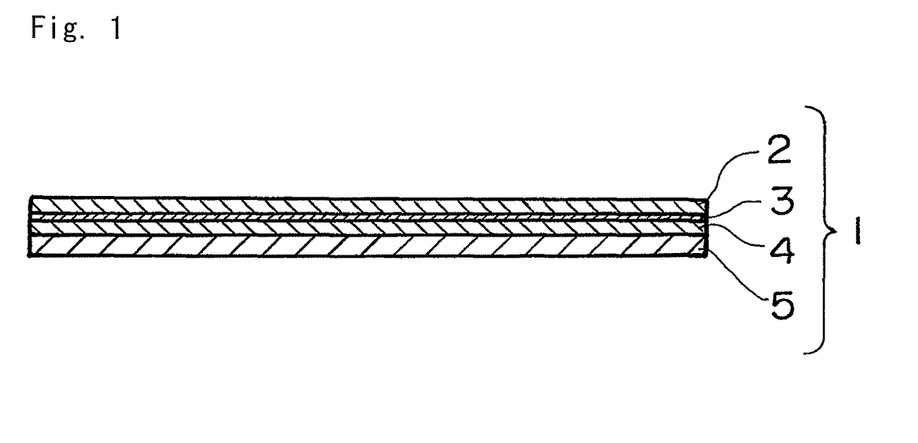
FIG. 1 is a schematic cross-sectional side view showing the basic structure of the tape preparation of the present invention.

FIG. 1 shows a schematic cross-sectional side view of the tape preparation provided by the present invention based on the above-mentioned structure.

Specifically, a tape preparation 1 of the present invention is a tape preparation produced by laminating a drug-containing adhesive layer 4 on the printed ink layer 3 side of a cover film 2 with printing thereon and covering the drug-containing adhesive layer 4 with a release film 5.

The tape preparation provided by the present invention will be described below by explaining each of the components.

As described above, the tape preparation 1 of the present invention is produced by using the printed ink layer 3 instead of a conventional backing layer. This printed ink layer 3 is provided by printing the printed ink layer 3 on the cover film 2 with a print ink. The printed ink layer 3 thus provided to the cover film 2 may be used as long as it has a composition in which the printed ink layer 3 peels off from the cover film 2 and becomes an independent printed ink layer 3.

Materials of cover film 2 as described above are not particularly limited. Plastic films such as polypropylene (PP), polyethylene terephthalate (PET), polyethylene (PE), and polystyrene (PS), a single material or a laminated complex of paper, synthetic paper, and synthetic resin, a laminate of aluminum foil or deposited film and the above-mentioned material, and moreover, the above-mentioned single material or complex material that had been subjected to corona treatment, or siliconization or fluorine coating, or embossing or matting may be used.

The method for producing films from the material for the cover film 2 may be any method. Specifically, the methods include an inflation method, a T-die method, a calendering method, a flow casting method, and the like, and are not particularly limited.

The shape of the cover film 2 in the tape preparation of the present invention is not particularly limited, either; however, in consideration of productivity and handling at the time of application, the cover film 2 is preferably designed to have the same size as the drug-containing adhesive layer (ointment layer) 4 or slightly larger than the drug-containing adhesive layer (ointment layer) 4 and is preferably designed to be smaller than the release film 5.

Furthermore, it is preferable to make an incision (slit) on the cover film 2 to make it easy to peel off the cover film 2 from the printed ink layer 3 after application of the tape preparation 1.

The thickness of the cover film 2 is about 12 µm to 200 µm. Preferably, the cover film 2 is formed so that the thickness thereof falls within 12 µm to 100 µm.

As the thickness of the cover film decreases below 12 µm, the cover film becomes more liable to break at the time of production due to its thinness, and furthermore, handling the cover film becomes more difficult when the cover film is peeled off from the printed ink layer 3 after application. Therefore, a cover film thinner than 12 µm is not preferable.

On the other hand, as the thickness of the cover film increases above 200 µm, handling the cover film becomes easier; however, a cover film thicker than 200 µm is not preferable since it results in increased cost.

On the back of the cover film 2 of the present invention, the printed ink layer 3, which replaces a conventional backing layer for the drug-containing adhesive layer (ointment layer) 4, is provided in a laminated manner.

Laminating means for this printed ink layer 3 is printing it on the cover film 2. Although such a printing method is not particularly limited, gravure printing, offset printing, flexographic printing, silk-screen printing, and the like are preferable.

As for the type of the ink used for printing, it is good to use an ink suitable for each of the printing methods. In the tape preparation 1 of the present invention, since the printed ink layer 3 is exposed as a surface after application, water resistance, oil resistance, alkali resistance, abrasion resistance, releasability, flexibility, and the like need to be taken into account. Moreover, chemical resistance also needs to be taken into account, because the printed ink layer 3 is in direct contact with the drug-containing adhesive layer (ointment layer) 4.

Specifically, it is preferable to coat and protect the colored ink layer 3 by printing a transparent ink or varnish having the above-mentioned resistances on the cover film 2 as a first printing onto the cover film 2.

Furthermore, resistance to the drug-containing adhesive layer (ointment layer) 4 can be ensured by coating the printed ink layer 3 in the same manner at the end of printing. Furthermore, this coating process has the advantage that a paper blocking phenomenon that occurs in rolling up the cover film 2 with printing thereon can be suppressed.

Although the thickness of the printed ink layer 3 is not particularly limited, the thickness is preferably about 1 to 100 µm, and in particular, about 2 to 10 µm.

In the tape preparation 1 of the present invention, the drug-containing adhesive layer (ointment layer) 4 is laminated on the printed ink layer 3 side of the above-mentioned cover film 2 with printing thereon.

Components of the base for the adhesive layer constituting this drug-containing adhesive layer (ointment layer) 4 are not particularly limited as long as the component can be a base for an adhesive agent layer, that is, the ointment composition. Thus, any base that is used in a conventional tape preparation can be adapted. Specifically, hydrophobic polymers such as rubber-based polymers, acrylic polymers, and silicon-based polymers are preferably used.

The tape preparation 1 of the present invention is configured by laminating the drug-containing adhesive layer 4 on the printed ink layer 3 side of the cover film 2 with printing thereon and covering the laminated drug-containing adhesive layer 4 with the release film 5.

Materials for the release film 5 that are used are not particularly limited. Plastic films such as polypropylene (PP), polyethylene terephthalate (PET), polyethylene (PE), and polystyrene (PS), a single material or a laminated complex of paper, synthetic paper, and synthetic resin, a laminate of aluminum foil or deposited film and the above-mentioned material, and the above-mentioned single material or complex material that had been subjected to corona treatment, or siliconization, fluorine coating, embossing, or matting, and moreover printing or coloring are used.

The method for producing films from the material for the release film 5 may be any method. Specifically, the methods include an inflation method, a T-die method, a calendering method, a flow casting method and the like, and are not particularly limited.

The shape of the release film 5 in the tape preparation 1 of the present invention is not particularly limited; however, in consideration of productivity and handling at the time of application, the release film 5 is preferably designed to be larger than the drug-containing adhesive layer 4 or the cover film 2. It is also preferable that the corners of the release film 5 be trimmed to prevent fingers from being injured.

It is also possible to display a letter, an arrow, a symbol, an illustration, and the like on the release film 5 or color the release film 5 in order to show clearly how to apply the tape preparation.

The thickness of the release film 5 in the present invention is about 12 µm to 200 µm. Preferably, the release film 5 is formed so that the thickness thereof falls within 38 µm to 150 µm. As the thickness of the release film decreases below 12 µm, the release film becomes more liable to wrinkle at the time of production due to its thinness. Therefore, a release film thinner than 12 µm is not preferable.

On the other hand, as the thickness of the release film increases above 200 µm, cost increases. Therefore, a release film thicker than 200 µm is not preferable.

Application of the tape preparation 1 of the present invention having the above-mentioned composition is, specifically, completed by peeling off the release film 5 and applying the exposed drug-containing adhesive layer 4 onto the targeted surface, and furthermore peeling off the cover film 2 from the tape preparation. Consequently, the printed ink layer 3 is exposed as a surface instead of a conventional backing layer for the drug-containing adhesive layer 4.

Therefore, to make such application easy, it is preferable that the adhesive strength between the cover film 2 and the printed ink layer 3 be higher than the adhesive strength between the drug-containing adhesive layer 4 and the release film 5, and the adhesive strength between the printed ink layer 3 and the drug-containing adhesive layer 4 be higher than the adhesive strength between the cover film 2 and the printed ink layer 3.

Therefore, in consideration of handling at the time of release, it is preferable that the release film 5 of the tape preparation 1 of the present invention have suitable rigidity and be subjected to processing to make its release easy. At the time of application of the tape preparation 1 of the present invention, by peeling off the release film 5, the drug-containing adhesive layer 4, which is expected to be the surface that is applied first, needs to be exposed. Therefore, the release film 5 has to be designed so that the release film 5 covers the drug-containing adhesive layer with a lower adhesive strength than both of the adhesive strength between the cover film 2 and the printed ink layer 3 and the adhesive strength between the printed ink layer 3 and the agent-containing adhesive layer 4.

Various drugs can be mixed in the drug-containing adhesive layer 4 of the tape preparation 1 provided by the present invention depending on the purpose of the tape preparation.

Specifically, indomethacin, ketoprofen, flurbiprofen, ibuprofen, felbinac, diclofenac, glycol salicylate, methyl salicylate, glycyrrhizic acid, dipotassium glycyrrhizinate, beta-glycyrrhizic acid, and the like can be mixed as an analgesic anti-inflammatory ingredient.

Furthermore, ingredients for promoting blood circulation include tocopherol acetic acid esters, Capsicum extract, capsaicin, nonylic acid vanillylamide, benzyl nicotinate, benzyl alcohol, and the like; antiallergic ingredients include diphenhydramine, chlorpheniramine maleate, and the like; local stimulation ingredients include l-menthol, camphor, mentha oil, eucalyptus oil, and the like; local anesthetic ingredients include lidocaine, benzocaine, dibucaine, tetracaine, and the like; antipruritic ingredients include crotamiton and the like; however, these ingredients are not limited thereto.

Two or more of these drugs may be used in combination as necessary.

The content of the drug to be mixed is selected as appropriate depending on the type and the purpose of a patch such as a tape preparation so that the predetermined effective dose may be applied onto the affected area at the time of application to a patient.

Needless to say, the tape preparation provided by the present invention is not limited to a tape preparation as described above as a medicine that includes only a drug and can also be applied to cosmetics such as various perfumes, moisturizing ingredients, whitening ingredients, and the like.

EXAMPLES

Herein below, embodiments of the present invention based on specific examples will be described with reference to the figures. However, the present invention is not limited to these examples and various modifications can be made without departing from the technical idea of the present invention.
<First Embodiment>

Figure 2:
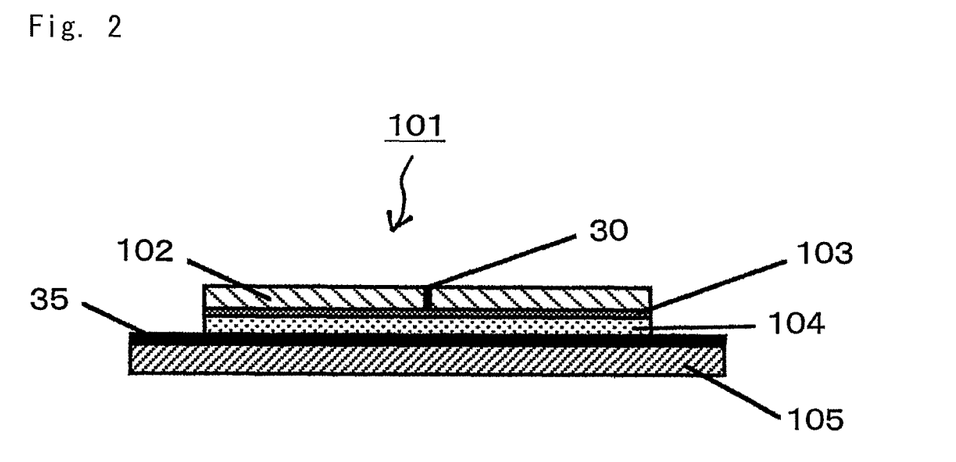
FIG. 2 is a schematic cross-sectional side view of the tape preparation according to a first embodiment of the present invention.

FIG. 2 is a schematic cross-sectional side view of a tape preparation 101 based on a first embodiment, which is a basic aspect of the tape preparation of the present invention.

Thus, the tape preparation 101 of the present invention is produced by sequentially laminating a drug-containing adhesive layer 104 on the printed ink layer 103 side of a cover film with printing thereon 102 and covering the drug-containing adhesive layer with a silicon-coated release film 105.

Specifically, siliconized (silicon-coated) 35 polyethylene terephthalate (PET) having a thickness of 75 μm was used as the release film 105; on the silicon-coated surface of the release film 105, an ointment composition containing crotamiton, lidocaine, and diphenhydramine was spread as the drug-containing adhesive layer (ointment layer) (shown as a drug layer in the figure); furthermore, matted stretched polypropylene (OPP) having a thickness of 40 μm was used as the cover film and the drug-containing adhesive layer (ointment layer) was covered by the printed ink surface that had been prepared by gravure printing on the whole surface of a transparent ink-printed surface; and the resulting product was used as a raw material.

Then, as the next step, the laminated material with the exception of the release film was die-cut into a circular piece having a diameter of 30 mm, a slit 30 was made only on the cover film layer 102 of the center of the circular piece, and then the remaining part surrounding the circular piece was removed to obtain an antipruritic patch.

The method of use of the antipruritic patch formed as described above is described, wherein the antipruritic patch is a specific embodiment, the first embodiment, of the present invention.

Figure 3:
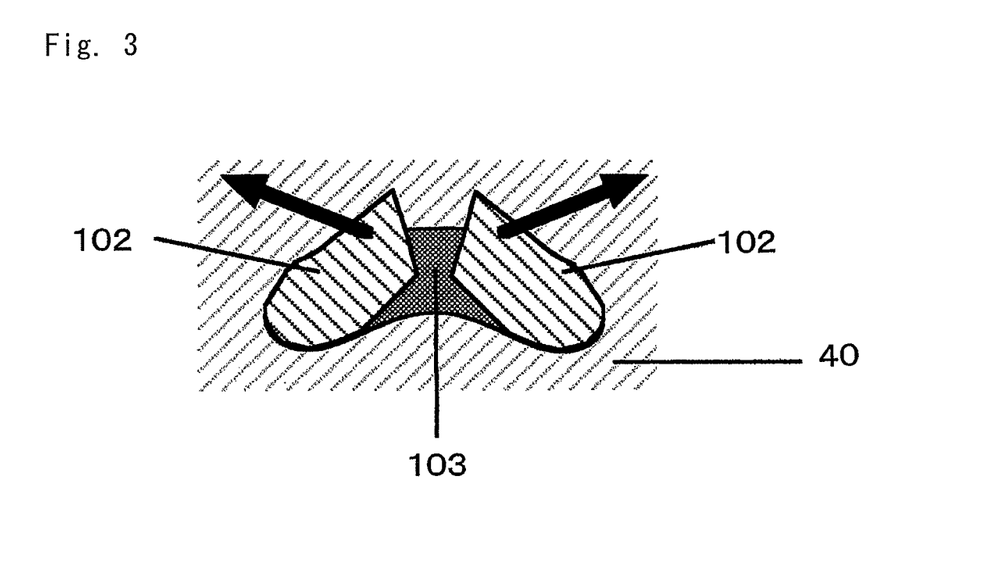
FIG. 3 is a schematic diagram showing how to peel off the cover film of the tape preparation according to the first embodiment of the present invention.

FIG. 3 shows a schematic diagram describing how to use the antipruritic patch.

As is shown in the figure, the release film 105 is firstly peeled off so that the drug-containing adhesive layer is exposed, and then the exposed layer is applied onto a targeted affected area (skin surface) 40. Then, the tape preparation that includes the circular drug-containing adhesive layer (drug layer) on which the cover film with printing thereon is laminated is pinched as if by sandwiching the ends of the tape preparation lightly between fingers. Consequently, the parts of the cover film 102 peel off from the slit part provided in the center (arrows in the figure). Then, each part of the cover film 102 is taken and peeled off. As a result, the printed ink layer 103 is exposed as a surface part. Thus, the application procedure of the tape preparation is completed.

Consequently, only the drug-containing adhesive layer and the printed ink layer 103 laminated thereon are applied onto the surface for application. Since the printed ink layer 103 is thinner than a conventional backing, the printed ink layer 103 does not inhibit the resilience and elasticity that the ointment layer has. Therefore, conformability at the application site becomes very good. Furthermore, when the printed ink layer 103 is transparent, the tape preparation does not stand out visually at all.

Furthermore, since the printed ink layer conforms to the elasticity of the ointment layer, the applied tape preparation can remain stable, that is, the tape preparation does not peel off from the application site.
<Second Embodiment>

Figure 4:
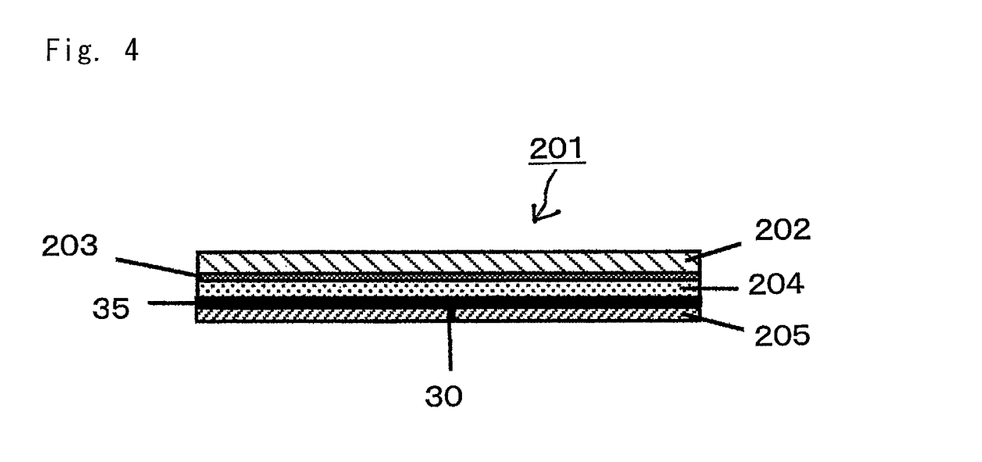
FIG. 4 is a schematic cross-sectional side view of the tape preparation according to a second embodiment of the present invention.

FIG. 4 shows a schematic cross-sectional side view of a tape preparation 201 based on a second embodiment, which is another basic aspect of the tape preparation of the present invention.

Thus, the tape preparation 201 of the present invention is also configured by sequentially laminating a drug-containing adhesive layer 204 on the printed ink layer 203 side of a cover film 202 with printing thereon and covering the drug-containing adhesive layer 204 with a silicon-coated 35 release film 205; however, in this example, a slit 30 is made in the center of the release film 205.

Specifically, siliconized (silicon-coated) polyethylene terephthalate (PET) having a thickness of 38 μm was used as the release film 205; on the silicon-coated surface side of the release film 205, an ointment composition containing indomethacin and l-menthol was spread as the drug-containing adhesive layer (ointment layer) 204 (shown as a drug layer in the figure); corona-treated stretched polypropylene having a thickness of 75 µm whose corona-treated surface had been subjected to silk-screen printing using a flexible ink was used as the cover film 202 and the drug layer 204 was covered by the printed ink layer 203; and the resulting product was used as a raw material.

Then, in the next step, the slit 30 was made on the release film 205 at its center, and the textile stuff was die-cut into a quadrangle 70 mm long and 100 mm broad to obtain an analgesic anti-inflammatory tape preparation.

The method of use of the analgesic anti-inflammatory tape preparation formed as described above is described, wherein the tape preparation is a specific embodiment, the second embodiment, of the present invention.

Figure 5:
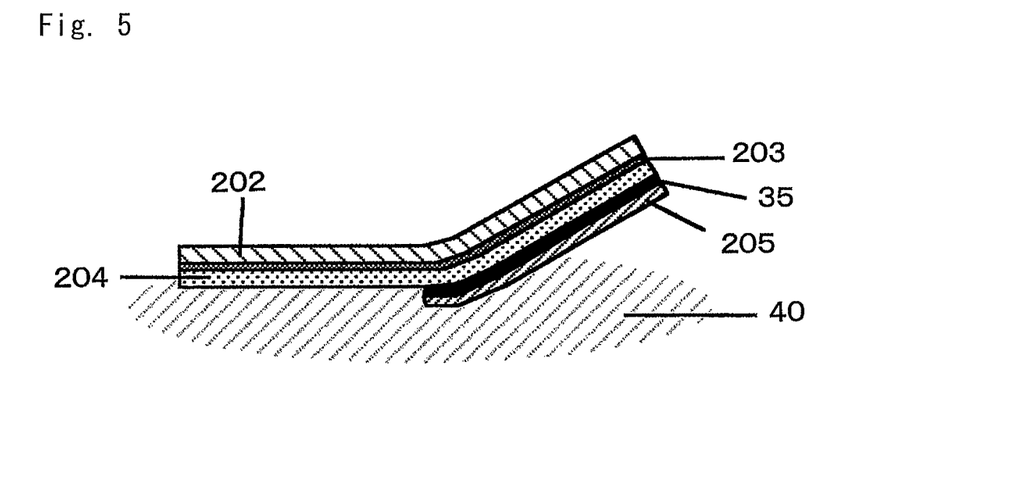
FIG. 5 is a schematic diagram showing the state of the tape preparation according to the second embodiment of the present invention when the tape preparation was applied onto an application site.

FIG. 5 shows a schematic diagram describing how to use the analgesic anti-inflammatory tape preparation.

As is shown in the figure, the release film 205 of the analgesic anti-inflammatory tape preparation is firstly bent outwards, and one of the two parts of the release film 205 is peeled off and removed.

Then, the tape preparation is temporarily stuck down by applying one part of the exposed ointment surface (drug layer) 204 onto an affected area (skin surface) 40. The remaining part of the release film 205 is also peeled off to expose the ointment surface (drug layer) 204. The exposed ointment surface (drug layer) 204 is attached by pressure, thereby applying the entire surface of the ointment onto the affected area.

Figure 6:
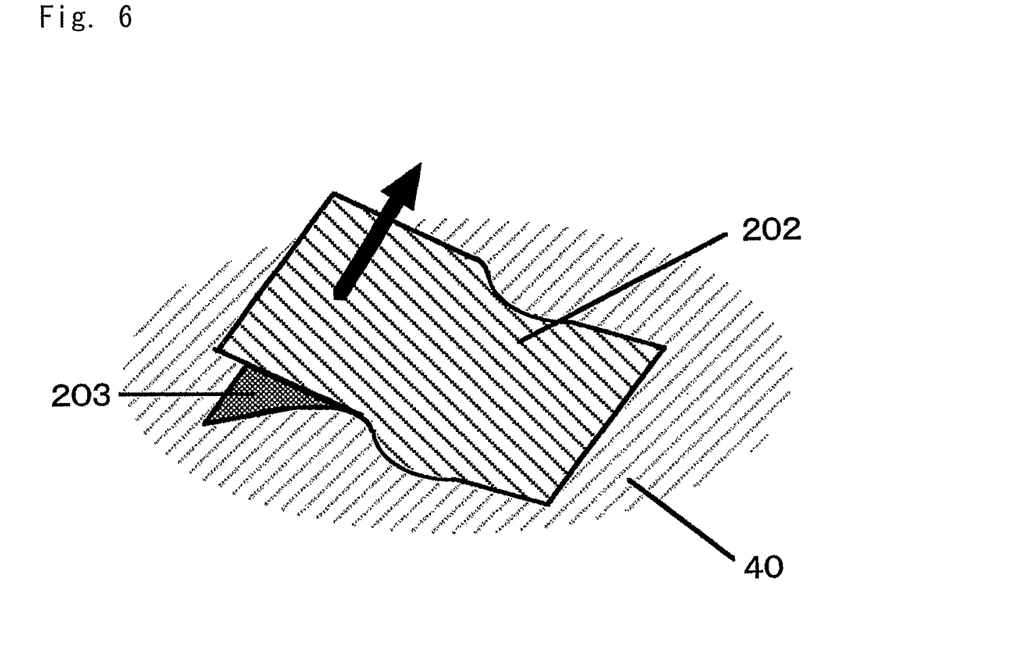
FIG. 6 is a schematic diagram showing how to peel off the cover film of the tape preparation according to the second embodiment of the present invention after the tape preparation was applied onto an application site.

FIG. 6 schematically shows how to peel off the cover sheet of the tape preparation afterwards. As is shown in the figure, when the end of the applied tape preparation is pinched as if by sandwiching it lightly between fingers, the cover film 202, which has a high rigidity, peels off from the end of the tape preparation (arrow in the figure); then, that part of the cover film 202 is grabbed and peeled off. As a result, the printed ink layer 203 is exposed as a surface part. Thus, the application procedure of the tape preparation is completed.

Also in this case, only the drug-containing adhesive layer and the printed ink layer laminated thereon are applied onto a surface for application. Since the printed ink layer is thinner than a conventional backing, the printed ink layer does not inhibit the resilience and elasticity that the ointment layer has. Therefore, conformability at the application site becomes very good.

Furthermore, since the printed ink layer conforms to the elasticity of the ointment layer, the applied tape preparation can remain stable, that is, the tape preparation does not peel off from the application site.

The tape preparation of the present invention and the method for applying the same described above with reference to the figures have been described based on the specific embodiments of the present invention. It is needless to say that many variations of the present invention may be devised and are encompassed within the technical scope of the present invention as long as the basic embodiment is a tape preparation produced by laminating a drug-containing adhesive layer on the printed ink layer side of a cover film with printing thereon and covering the drug-containing adhesive layer with a release film.

Industrial Applicability

As described above, the present invention provides a very good tape preparation with excellent conformability that is produced by laminating a drug-containing adhesive layer on a cover film with printing thereon instead of a conventional backing, so that a printed ink layer of the cover film with printing thereon serves as a covering layer for the applied drug-containing adhesive layer.

The tape preparation provided by the present invention has the above-mentioned effect and its industrial advantage is great.

Reference Signs List

| 1, 101, 201 | tape preparation |
| 2, 102, 202 | cover film |
| 3, 103, 203 | printed ink layer |
| 4, 104, 204 | drug-containing adhesive layer |
| 5, 105, 205 | release film |
| 30 | slit |
| 35 | silicon layer |

The invention claimed is:

1. A tape preparation comprising a drug-containing adhesive layer, a cover film, a printed ink layer, and a release film, the printed ink layer configured to serve as a single layer cover layer for the drug-containing adhesive layer, wherein the cover film is laminated to one side of the printed ink layer and the drug-containing adhesive layer is laminated on the other side of the printed ink layer and wherein the drug-containing adhesive layer is covered with the release film and wherein adhesive strength between the cover film and the printed ink layer is higher than an adhesive strength between the drug-containing adhesive layer and the release film, and an adhesive strength between the printed ink layer and the drug-containing adhesive layer is higher than an adhesive strength between the cover film and the printed ink layer, and wherein the printed ink layer serves as a covering for the drug-containing adhesive layer.

2. A method of applying the tape preparation according to claim 1 to an application site, comprising peeling off the release film and applying the drug-containing adhesive layer of the tape preparation to the application site, and then peeling off the cover film from the printed ink layer wherein the drug-containing adhesive layer is applied onto the application site in such a manner that the printed ink layer is still laminated on the drug-containing adhesive layer.

3. The tape preparation according to claim 1, wherein a slit is provided on the cover film and/or the release film.

4. The tape preparation according to claim 1, wherein the tape preparation is produced by laminating the drug-containing adhesive layer on the printed ink layer and covering the drug-containing adhesive layer with the release film.

5. The tape preparation according to claim 1, wherein a slit is provided on the cover film and/or the release film.

6. The method according to claim 2, wherein a slit is provided on the cover film and/or the release film.

7. The tape preparation according to claim 1, wherein the tape preparation is produced by laminating the drug-containing adhesive layer on the printed ink layer and covering the drug-containing adhesive layer with the release film.

8. The tape preparation according to claim 3, wherein the tape preparation is produced by laminating the drug-containing adhesive layer on the printed ink layer and covering the drug-containing adhesive layer with the release film.

9. A method for applying the tape preparation according to claim 3 to a targeted site, comprising peeling off the release film and applying the drug-containing adhesive layer onto the targeted surface, and then peeling off the cover film.

* * * * *